United States Patent [19]

Maeda et al.

[11] Patent Number: 5,773,247
[45] Date of Patent: Jun. 30, 1998

[54] RECOMBINANT ANTI-HIV ANTIBODY AND PROCESS FOR PREPARING THE SAME

[75] Inventors: Hiroaki Maeda; Kazuhiko Kimachi; Yasuyuki Eda; Kouichi Shiosaki; Kiyoshi Osatomi; Sachio Tokiyoshi, all of Kumamoto, Japan

[73] Assignee: Juridical Foundation The Chemo-Sero-Therapeutic Research Institute, Kumamoto, Japan

[21] Appl. No.: 491,845

[22] PCT Filed: Jan. 14, 1993

[86] PCT No.: PCT/JP93/00039

§ 371 Date: Jul. 14, 1995

§ 102(e) Date: Jul. 14, 1995

[87] PCT Pub. No.: WO94/15969

PCT Pub. Date: Jul. 12, 1994

[51] Int. Cl.[6] .............................. C12P 21/06; C12P 21/08; C12N 5/00; C07H 21/04
[52] U.S. Cl. ................................... 435/69.1; 435/240.27; 530/387.3; 530/388.35; 536/231
[58] Field of Search .............................. 435/69.1, 240.27; 530/387.3, 388.35; 536/23.1

[56] References Cited

FOREIGN PATENT DOCUMENTS

| 0125023 | 11/1984 | European Pat. Off. . |
|---|---|---|
| 0171496 | 2/1986 | European Pat. Off. . |
| 0239400 | 9/1987 | European Pat. Off. . |
| 0327000 | 8/1989 | European Pat. Off. . |
| 0465979 | 1/1992 | European Pat. Off. . |

OTHER PUBLICATIONS

Saiki, Randall k. et al., "Primer–Directed enzymatic amplification of DNA with a thermostable DNA polymerase. "Science vol. 239, pp. 487–491 (29 Jan. 1988).

Larosa, Grefory J. et al., "Conserved sequence and structural elements in the HIV–1 principal neutralizing determinant. "Science vol. 249, pp. 932–935 (24 Aug. 1995).

Orlandi, Rosaria, et al., "Cloning immunoglobin variable domains for expression by the polymerase chain reaction. "PROC. NATL. ACAD. SCI., USA vol. 86, pp. 3833–3837 (May 1989).

(List continued on next page.)

*Primary Examiner*—Ponnathapura Achutamurthy
*Assistant Examiner*—Hankyel T. Park
*Attorney, Agent, or Firm*—Browdy and Neimark

[57] ABSTRACT

The present invention relates to a gene fragment coding for a variable region of an antibody having a neutralizing activity against human immunodeficiency virus (HIV) and a process for preparing the same. A mouse-human chimeric antibody and a mouse-human reshaped antibody having a neutralizing activity against HIV can be prepared by obtaining a specific nucleotide sequence of a gene fragment coding for a variable region of H chain and L chain of an antibody having a neutralizing activity against HIV, and then artificially fusing DNAs synthesized based on these nucleotide sequences with a gene coding for a human immunoglobulin. The novel recombinant anti-HIV antibody of the present invention is useful for treatment and prevention of AIDS.

10 Claims, 12 Drawing Sheets

```
          |  FR1
     1  CAGATCCAGATGGTGCAGTCTGGACCTGAGTTGAAGAAGCCTGGAGAGACAGTCAAGATC
        GlnIleGlnMetValGlnSerGlyProGluLeuLysLysProGlyGluThrValLysIle

|   CDR1        |   FR2
    61  TCCTGCAAGGCTTCTGGGTATACCTTCACAAAATATGGAATGAACTGGGTGAAACAGACT
        SerCysLysAlaSerGlyTyrThrPheThrLysTyrGlyMetAsnTrpValLysGlnThr

|  CDR2
   121  CCAGGAAAGGGTTTAAAGTGGATGGGCTGGAAAAACACCAATACTGGAGAGTCAACACAT
        ProGlyLysGlyLeuLysTrpMetGlyTrpLysAsnThrAsnThrGlyGluSerThrHis

|  FR3
   181  GTTGAAGAGTTCAAGGGACGGTTTGCCTTCTCTTTGCAAACCTCTGCCAGTACTGCCTAT
        ValGluGluPheLysGlyArgPheAlaPheSerLeuGluThrSerAlaSerThrAlaTyr

|
   241  TTGCAGATCAACAACCTCAAAAATGAGGACACGGCTACATATTTCTGTGCAAGAGAATAT
        LeuGlnIleAsnAsnLeuLysAsnGluAspThrAlaThrTyrPheCysAlaArgGluTyr

CDR3                    |   FR4
   301  GATTACGACGGGGGCTTTTCTTACTGGGGCCAAGGGACTCTGGTCACTGTCTCTGCA
        AspTyrAspGlyGlyPheSerTyrTrpGlyGlnGlyThrLeuValThrValSerAla
```

OTHER PUBLICATIONS

Huse, Willaim D. et al., "Generation of a large combinatorial library of the immunoglobin repertoire in phage lambda." Science vol 246, pp. 1275–1281 08 December 1989).

Waldmann, H. ed., et al., "Novel antibodies by DNA manipulation." Monoclonal Antibody Therapy Prog Allergy vol. 45, pp. 91–105 (1988).

Morrison, Sherie l. et al., "Genetically engineered antibody molecules." Advances in Immunology vol. 44, pp. 65–92 (1989).

Whittle, Nigel et al., "Expression in COS cells of mouse–human chimaeric B72.3 antibody." Protein Engineering vol. 1, No. 6 pp. 449–505 (1987).

Nishimura, Yushi et al., "Recombinant human–mouse chimeric monoclonal antibody specific for common acute lymphocytic leukemia antigen." Cancer Research vol. 47, pp. 999–1005 (15 Feb. 1987).

Guroff, Marjorie Robert et al., "HTLV–III neutralizing antibody development in transfusion–dependent seropositive patients with B–thalassemia." The Journal of Immunology vol. 138, No. 11, pp. 3731–3736 (01 Jun. 1987).

Glover D.M. ed., "Construction and screening cDNA libraries in (Lambda)λgt 10 and (Lambda)λgt 11." DNA Cloning vol I. Chapter 2, IRL Press, Washington, D.C. (1980).

Honjo, Tasuku, "Immunoglobulin genes."Ann. Rev. Immunology vol. 1, pp. 499–528 (1983).

Tonegawa, Susumu, "Somatic generation of antibody diversity." Nature vol. 302 pp. 575–581, (14 Apr 1983).

Moaniatis, T. et al., "Construction of genomic libraries in bacteriophage (Lambda)λvectors."Molecular Cloning: A Laboratory Manual pp. 270–307 (1982).

Max, Edward E. et al., "The nucleotide sequence of a 5.5–kilobase DNA segment containing the mouse (Kappa)κ immunoglobulin in J and C region genes. "Biological Chemistry vol. 256, pp. 5116–5120, (1981).

Sakano, Hitoshi, et al., "Two types of somatic recombinant are necessary for the generation of complete immunoglobul in heavy–chain genes."Nature vol. 286 pp. 676–683 (14 Aug. 1980).

Palm, Walter et al., "Die Primarstruktur einer kristallinen monoklonalen immunoglobulin in–L–kette vom (Kappa)κ–typ, subgruppe I (Bence–Jones–Protein Rei.), isolierung und charakerisierung der tryptischen peptide; die vollstandige aminosauresequenz des proteins."Physi. Chem. vol. 356, pp. 167–191 (1975).

"Sequences of proteins of immunological interest, 4th." U.S. Department of Health and Human Services. (1987).

FIG. 1

```
      | FR1
  1 CAGATCCAGATGGTGCAGTCTGGACCTGAGTTGAAGAAGCCTGGAGAGACAGTCAAGATC
    GlnIleGlnMetValGlnSerGlyProGluLeuLysLysProGlyGluThrValLysIle

|   CDR1      |   FR2
 61 TCCTGCAAGGCTTCTGGGTATACCTTCACAAAATATGGAATGAACTGGGTGAAACAGACT
    SerCysLysAlaSerGlyTyrThrPheThrLysTyrGlyMetAsnTrpValLysGlnThr

|   CDR2
121 CCAGGAAAGGGTTTAAAGTGGATGGGCTGGAAAAACACCAATACTGGAGAGTCAACACAT
    ProGlyLysGlyLeuLysTrpMetGlyTrpLysAsnThrAsnThrGlyGluSerThrHis

|  FR3
181 GTTGAAGAGTTCAAGGGACGGTTTGCCTTCTCTTTGGAAACCTCTGCCAGTACTGCCTAT
    ValGluGluPheLysGlyArgPheAlaPheSerLeuGluThrSerAlaSerThrAlaTyr

|
241 TTGCAGATCAACAACCTCAAAAATGAGGACACGGCTACATATTTCTGTGCAAGAGAATAT
    LeuGlnIleAsnAsnLeuLysAsnGluAspThrAlaThrTyrPheCysAlaArgGluTyr

CDR3                     |   FR4
301 GATTACGACGGGGGCTTTTCTTACTGGGGCCAAGGGACTCTGGTCACTGTCTCTGCA
    AspTyrAspGlyGlyPheSerTyrTrpGlyGlnGlyThrLeuValThrValSerAla
```

FIG. 2

```
    | FR1
  1 GACATTGTGATGACCCAGTCTCACAAATTCATGTCCACATCAGTAGGAGACAGGGTCAGC
    AspIleValMetThrGlnSerHisLysPheMetSerThrSerValGlyAspArgValSer

| CDR1                                    | FR2
 61 ATCACCTGCAAGGCCAGTCAGGATGTGGGTGCTGATGTAGCCTGGTATCAACAGAAACCA
    IleThrCysLysAlaSerGlnAspValGlyAlaAspValAlaTrpTyrGlnGlnLysPro

| CDR2            | FR3
121 GGACAATCTCCTAAACAACTGATTTCCTGGGCATCCACCCGGCACACTGGAGTCCCTGAT
    GlyGlnSerProLysGlnLeuIleSerTrpAlaSerThrArgHisThrGlyValProAsp

181 CGCTTCACAGGCAGTGGATCTGGGACAGATTTCACTCTCACCATTACCAATGTGCAGTCT
    ArgPheThrGlySerGlySerGlyThrAspPheThrLeuThrIleThrAsnValGlnSer

| CDR3                    | FR4
241 GAAGACTTGGCAGATTATTTCTGTCAGCAATATAGCAGCTTTCCTCTCACGTTCGGTACT
    GluAspLeuAlaAspTyrPheCysGlnGlnTyrSerSerPheProLeuThrPheGlyThr

301 GGGACCAAGTTGGAGCTGAGA
    GlyThrLysLeuGluLeuArg
```

FIG. 3

```
     | FR1
  1  GAGGTCCAGCTGCAACAGTCTGGGCCTGACCTGGTGAAGCCTGGGGCTTCAGTGAAGATA
     GluValGlnLeuGlnGlnSerGlyProAspLeuValLysProGlyAlaSerValLysIle

|   CDR1         |    FR2
 61  TCCTGCAAGACTTCTGGATACACATTCACTGAATACACCATGCACTGGGTGAAGCAGAGC
     SerCysLysThrSerGlyTyrThrPheThrGluTyrThrMetHisTrpValLysGlnSer

|   CDR2
121  CATGGAAGGAGCCTTGAGTGGATTGGAGGTATTAATCCTAACAATGGTGATACTAGCTAC
     HisGlyArgSerLeuGluTrpIleGlyGlyIleAsnProAsnAsnGlyAspThrSerTyr

|   FR3
161  ACCCAGAAGTTCAAGGGCAAGGCCACATTGACTGTAGACAAGTCCTCCAGCACAGCCTAC
     ThrGlnLysPheLysGlyLysAlaThrLeuThrValAspLysSerSerSerThrAlaTyr

|
241  ATGGAGCTCCGCAGCCTGACATCTGAGGATTCTGCAGTCTATTACTGTGCAACACCCTAC
     MetGluLeuArgSerLeuThrSerGluAspSerAlaValTyrTyrCysAlaThrProTyr

CDR3              |    FR4
301  TATGCCTATGCTATTGACTCCTGGGGTCAAGGAACCTCAGTCACCGTCTCCTCA
     TyrAlaTyrAlaIleAspSerTrpGlyGlnGlyThrSerValThrValSerSer
```

FIG. 4

```
   | FR1
 1 GACATTGTGCTGACCCAATCTCCAGCTTCTTTGGCTGTGTCTCTAGGGCAGAGGGCCACC
   AspIleValLeuThrGlnSerProAlaSerLeuAlaValSerLeuGlyGlnArgAlaThr

|   CDR1                                       |   FR2
61 ATCTCCTGCAAGGCCAGCCAAAGTGTTGATTATGATGGTGATAGTTATATGAACTGGTAC
   IleSerCysLysAlaSerGlnSerValAspTyrAspGlyAspSerTyrMetAsnTrpTyr

|   CDR2
121 CAACAGAAACCAGGACAGCCACCCAAACTCCTCATCTATGCTGCATCCAATCTAGAATCT
    GlnGlnLysProGlyGlnProProLysLeuLeuIleTyrAlaAlaSerAsnLeuGluSer

|  FR3
181 GGGATCCCAGCCAGGTTTAGTGGCAGTGGGTCTGGGACAGACTTCACCCTCAACATCCAT
    GlyIleProAlaArgPheSerGlySerGlySerGlyThrAspPheThrLeuAsnIleHis

|  CDR3
241 CCTGTCGAGGAGGAGGATGGTGCAACCTATTACTGTCAGCAAAGTAATGAGGATCCGTGG
    ProValGluGluGluAspGlyAlaThrTyrTyrCysGlnGlnSerAsnGluAspProTrp

| FR4
301 ACGTTCGGTGGAGGCACCAAGCTGGAAATCAAA
    ThrPheGlyGlyGlyThrLysLeuGluIleLys
```

■ Mouse VL gene fragment
□ Human Cκ gene fragment
▨ HCMV
▨ pSV2neo

FIG. 9

```
    | FR1
  1 CAGGTGCAACTAGTGCAGTCCGGCGCCGAAGTGAAGAAACCCGGTGCTTCCGTGAAGGTG
    GlnValGlnLeuValGlnSerGlyAlaGluValLysLysProGlyAlaSerValLysVal

|    CDR1      |   FR2
 61 AGCTGTAAAGCTAGCGGTTATACCTTCACAAAATATGGAATGAACTGGGTTAGACAGGCC
    SerCysLysAlaSerGlyTyrThrPheThrLysTyrGlyMetAsnTrpValArgGlnAla

|    CDR2
121 CCAGGCCAAGGGCTCAAGTGGATGGGCTGGAAAAACACCAATACTGGAGAGTCAACACAT
    ProGlyGlnGlyLeuLysTrpMetGlyTrpLysAsnThrAsnThrGlyGluSerThrHis

|   FR3
181 GTTGAGGAGTTTAAGGGCAGGGTTACCATGTCCTTGGACACCTCTACAAACACCGCCTAC
    ValGluGluPheLysGlyArgValThrMetSerLeuAspThrSerThrAsnThrAlaTyr

|
241 ATGGAACTGTCCAGCCTGCGCTCCGAGGACACTGCAGTTTACTACTGCGCCAGAGAATAT
    MetGluLeuSerSerLeuArgSerGluAspThrAlaValTyrTyrCysAlaArgGluTyr

CDR3                 |   FR4
301 GATTACGACGGGGGCTTCTCCTATTGGGGACAGGGTACCCTTGTCACCGTCAGTTCA
    AspTyrAspGlyGlyPheSerTyrTrpGlyGlnGlyThrLeuValThrValSerSer
```

FIG. 10

```
    | FR1
  1 GACATCCAGATGACCCAGAGCCCAAGCAGCCTGAGCGCCAGCGTGGGTGACAGAGTGACC
    AspIleGlnMetThrGlnSerProSerSerLeuSerAlaSerValGlyAspArgValThr

| CDR1                                  | FR2
 61 ATCACCTGTAAAGCCAGCCAGGATGTGGGTGCTGATGTAGCTTGGTACCAGCAGAAGCCA
    IleThrCysLysAlaSerGlnAspValGlyAlaAspValAlaTrpTyrGlnGlnLysPro

| CDR2              | FR3
121 GGTAAGGCTCCAAAGCTGCTGATCTCCTGGGCATCCACCCGGCACACTGGTGTGCCAAGC
    GlyLysAlaProLysLeuLeuIleSerTrpAlaSerThrArgHisThrGlyValProSer

181 AGATTCAGCGGTAGCGGTAGCGGTACCGACTTCACCTTCACCATCAGCAGCCTCCAGCCA
    ArgPheSerGlySerGlySerGlyThrAspPheThrPheThrIleSerSerLeuGlnPro

| CDR3                        | FR4
241 GAGGACATCGCCACATACTACTGCCAACAATATAGCAGCTTTCCACTCACGTTCGGCCAA
    GluAspIleAlaThrTyrTyrCysGlnGlnTyrSerSerPheProLeuThrPheGlyGln

301 GGGACCAAGGTGGAAATCAAA
    GlyThrLysValGluIleLys
```

FIG. 11

```
     |   FR1
   1 CAGGTGCAACTAGTGCAGTCCGGCGCCGAAGTGAAGAAACCCGGTGCTTCCGTGAAGGTG
     GlnValGlnLeuValGlnSerGlyAlaGluValLysLysProGlyAlaSerValLysVal

|   CDR1        |   FR2
  61 AGCTGTAAAGCTAGCGGTTATACCTTCACTGAATACACCATGCATTGGGTTAGACAGGCC
     SerCysLysAlaSerGlyTyrThrPheThrGluTyrThrMetHisTrpValArgGlnAla

|   CDR2
 121 CCAGGCCAAGGGCTCGAGTGGATTGGCGGTATTAACCCTAACAATGGCGATACAAGCTAT
     ProGlyGlnGlyLeuGluTrpIleGlyGlyIleAsnProAsnAsnGlyAspThrSerTyr

|   FR3
 181 ACCCAGAAGTTTAAGGGCAAGGCTACCATGACCGTAGACACCTCTACAAACACCGCCTAC
     ThrGlnLysPheLysGlyLysAlaThrMetThrValAspThrSerThrAsnThrAlaTyr

|
 241 ATGGAACTGTCCAGCCTGCGCTCCGAGGACACTGCAGTTTACTACTGCGCCACACCCTAC
     MetGluLeuSerSerLeuArgSerGluAspThrAlaValTyrTyrCysAlaThrProTyr

CDR3              |   FR4
 301 TACGCCTACGCTATTGACTCCTGGGGACAGGGTACCCTTGTCACCGTCAGTTCA
     TyrAlaTyrAlaIleAspSerTrpGlyGlnGlyThrLeuValThrValSerSer
```

FIG. 12

```
     |   FR1
  1  GACATCCAGATGACCCAGAGCCCAAGCAGCCTGAGCGCCAGCGTGGGTGACAGAGTGACC
     AspIleGlnMetThrGlnSerProSerSerLeuSerAlaSerValGlyAspArgValThr

|   CDR1                                      |   FR2
  61 ATCACCTGTAAGGCCAGCCAAAGTGTTGATTATGATGGTGATAGTTATATGAACTGGTAC
     IleThrCysLysAlaSerGlnSerValAspTyrAspGlyAspSerTyrMetAsnTrpTyr

|   CDR2
 121 CAGCAGAAGCCAGGTAAGGCTCCAAAGCTGCTGATCTACGCTGCATCCAATCTAGAATCT
     GlnGlnLysProGlyLysAlaProLysLeuLeuIleTyrAlaAlaSerAsnLeuGluSer

|   FR3
 181 GGTGTGCCAAGCAGATTCAGCGGTAGCGGTAGCGGTACCGACTTCACCTTCACCATCAGC
     GlyValProSerArgPheSerGlySerGlySerGlyThrAspPheThrPheThrIleSer

|   CDR3
 241 AGCCTCCAGCCAGAGGACATCGCCACCTACTACTGCCAGCAAAGTAATGAGGACCCATGG
     SerLeuGlnProGluAspIleAlaThrTyrTyrCysGlnGlnSerAsnGluAspProTrp

|   FR4
 301 ACGTTCGGCCAAGGGACCAAGGTGGAAATCAAA
     ThrPheGlyGlnGlyThrLysValGluIleLys
``` ns5,773,247

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..357

( x i ) SEQUENCE DESCRIPTION: SEQ ID NO:1:

```
CAG  ATC  CAG  ATG  GTG  CAG  TCT  GGA  CCT  GAG  TTG  AAG  AAG  CCT  GGA  GAG         48
Gln  Ile  Gln  Met  Val  Gln  Ser  Gly  Pro  Glu  Leu  Lys  Lys  Pro  Gly  Glu
 1              5                        10                       15

ACA  GTC  AAG  ATC  TCC  TGC  AAG  GCT  TCT  GGG  TAT  ACC  TTC  ACA  AAA  TAT         96
Thr  Val  Lys  Ile  Ser  Cys  Lys  Ala  Ser  Gly  Tyr  Thr  Phe  Thr  Lys  Tyr
               20                        25                       30

GGA  ATG  AAC  TGG  GTG  AAA  CAG  ACT  CCA  GGA  AAG  GGT  TTA  AAG  TGG  ATG        144
Gly  Met  Asn  Trp  Val  Lys  Gln  Thr  Pro  Gly  Lys  Gly  Leu  Lys  Trp  Met
          35                        40                       45

GGC  TGG  AAA  AAC  ACC  AAT  ACT  GGA  GAG  TCA  ACA  CAT  GTT  GAA  GAG  TTC        192
Gly  Trp  Lys  Asn  Thr  Asn  Thr  Gly  Glu  Ser  Thr  His  Val  Glu  Glu  Phe
     50                        55                       60

AAG  GGA  CGG  TTT  GCC  TTC  TCT  TTG  GAA  ACC  TCT  GCC  AGT  ACT  GCC  TAT        240
Lys  Gly  Arg  Phe  Ala  Phe  Ser  Leu  Glu  Thr  Ser  Ala  Ser  Thr  Ala  Tyr
65                        70                       75                       80

TTG  CAG  ATC  AAC  AAC  CTC  AAA  AAT  GAG  GAC  ACG  GCT  ACA  TAT  TTC  TGT        288
Leu  Gln  Ile  Asn  Asn  Leu  Lys  Asn  Glu  Asp  Thr  Ala  Thr  Tyr  Phe  Cys
                    85                       90                       95

GCA  AGA  GAA  TAT  GAT  TAC  GAC  GGG  GGC  TTT  TCT  TAC  TGG  GGC  CAA  GGG        336
Ala  Arg  Glu  Tyr  Asp  Tyr  Asp  Gly  Gly  Phe  Ser  Tyr  Trp  Gly  Gln  Gly
               100                      105                      110

ACT  CTG  GTC  ACT  GTC  TCT  GCA                                                     357
Thr  Leu  Val  Thr  Val  Ser  Ala
               115
```

( 2 ) INFORMATION FOR SEQ ID NO:2:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Gln Ile Gln Met Val Gln Ser Gly Pro Glu Leu Lys Lys Pro Gly Glu
 1               5                  10                  15
Thr Val Lys Ile Ser Cys Lys Ala Ser Gly Tyr Thr Phe Thr Lys Tyr
            20                  25                  30
Gly Met Asn Trp Val Lys Gln Thr Pro Gly Lys Gly Leu Lys Trp Met
        35                  40                  45
Gly Trp Lys Asn Thr Asn Thr Gly Glu Ser Thr His Val Glu Glu Phe
    50                  55                  60
Lys Gly Arg Phe Ala Phe Ser Leu Glu Thr Ser Ala Ser Thr Ala Tyr
 65                 70                  75                  80
Leu Gln Ile Asn Asn Leu Lys Asn Glu Asp Thr Ala Thr Tyr Phe Cys
                85                  90                  95
Ala Arg Glu Tyr Asp Tyr Asp Gly Gly Phe Ser Tyr Trp Gly Gln Gly
            100                 105                 110
Thr Leu Val Thr Val Ser Ala
            115
```

( 2 ) INFORMATION FOR SEQ ID NO:3:

( i ) SEQUENCE CHARACTERISTICS:
        ( A ) LENGTH: 321 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..321

( x i ) SEQUENCE DESCRIPTION: SEQ ID NO:3:

```
GAC ATT GTG ATG ACC CAG TCT CAC AAA TTC ATG TCC ACA TCA GTA GGA      48
Asp Ile Val Met Thr Gln Ser His Lys Phe Met Ser Thr Ser Val Gly
 1               5                  10                  15

GAC AGG GTC AGC ATC ACC TGC AAG GCC AGT CAG GAT GTG GGT GCT GAT      96
Asp Arg Val Ser Ile Thr Cys Lys Ala Ser Gln Asp Val Gly Ala Asp
            20                  25                  30

GTA GCC TGG TAT CAA CAG AAA CCA GGA CAA TCT CCT AAA CAA CTG ATT     144
Val Ala Trp Tyr Gln Gln Lys Pro Gly Gln Ser Pro Lys Gln Leu Ile
        35                  40                  45

TCC TGG GCA TCC ACC CGG CAC ACT GGA GTC CCT GAT CGC TTC ACA GGC     192
Ser Trp Ala Ser Thr Arg His Thr Gly Val Pro Asp Arg Phe Thr Gly
    50                  55                  60

AGT GGA TCT GGG ACA GAT TTC ACT CTC ACC ATT ACC AAT GTG CAG TCT     240
Ser Gly Ser Gly Thr Asp Phe Thr Leu Thr Ile Thr Asn Val Gln Ser
 65                 70                  75                  80

GAA GAC TTG GCA GAT TAT TTC TGT CAG CAA TAT AGC AGC TTT CCT CTC     288
Glu Asp Leu Ala Asp Tyr Phe Cys Gln Gln Tyr Ser Ser Phe Pro Leu
                85                  90                  95                 100

ACG TTC GGT ACT GGG ACC AAG TTG GAG CTG AGA                         321
Thr Phe Gly Thr Gly Thr Lys Leu Glu Leu Arg
```

(2) INFORMATION FOR SEQ ID NO:4:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:4:

```
Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Gly Ala Asp
             20                  25                  30

Val Ala Trp Tyr Gln Gln Lys Pro Gly Gln Ser Pro Lys Gln Leu Ile
         35                  40                  45

Ser Trp Ala Ser Thr Arg His Thr Gly Val Pro Asp Arg Phe Thr Gly
     50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Ser Ser Phe Pro Leu
                 85                  90                  95

Thr Phe Gly Thr Gly Thr Lys Leu Glu Leu Arg
                100                 105
```

(2) INFORMATION FOR SEQ ID NO:5:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..354

(xi) SEQUENCE DESCRIPTION: SEQ ID NO:5:

```
GAG GTC CAG CTG CAA CAG TCT GGG CCT GAC CTG GTG AAG CCT GGG GCT      48
Glu Val Gln Leu Gln Gln Ser Gly Pro Asp Leu Val Lys Pro Gly Ala
 1               5                  10                  15

TCA GTG AAG ATA TCC TGC AAG ACT TCT GGA TAC ACA TTC ACT GAA TAC      96
Ser Val Lys Ile Ser Cys Lys Thr Ser Gly Tyr Thr Phe Thr Glu Tyr
             20                  25                  30

ACC ATG CAC TGG GTG AAG CAG AGC CAT GGA AGG AGC CTT GAG TGG ATT     144
Thr Met His Trp Val Lys Gln Ser His Gly Arg Ser Leu Glu Trp Ile
         35                  40                  45

GGA GGT ATT AAT CCT AAC AAT GGT GAT ACT AGC TAC ACC CAG AAG TTC     192
Gly Gly Ile Asn Pro Asn Asn Gly Asp Thr Ser Tyr Thr Gln Lys Phe
     50                  55                  60

AAG GGC AAG GCC ACA TTG ACT GTA GAC AAG TCC TCC AGC ACA GCC TAC     240
Lys Gly Lys Ala Thr Leu Thr Val Asp Lys Ser Ser Ser Thr Ala Tyr
65                  70                  75                  80

ATG GAG CTC CGC AGC CTG ACA TCT GAG GAT TCT GCA GTC TAT TAC TGT     288
Met Glu Leu Arg Ser Leu Thr Ser Glu Asp Ser Ala Val Tyr Tyr Cys
                 90                  95                  100

GCA ACA CCC TAC TAT GCC TAT GCT ATT GAC TCC TGG GGT CAA GGA ACC     336
Ala Thr Pro Tyr Tyr Ala Tyr Ala Ile Asp Ser Trp Gly Gln Gly Thr
                105                 110                 115
```

```
TCA GTC ACC GTC TCC TCA                                                                                         354
Ser Val Thr Val Ser Ser
            120
```

(2) INFORMATION FOR SEQ ID NO:6:

(i) SEQUENCE CHARACTERISTICS:
      (A) LENGTH: 118 amino acids
      (B) TYPE: amino acid
      (D) TOPOLOGY: linear (ii) MOLECULE TYPE: protein (xi) SEQUENCE DESCRIPTION: SEQ ID NO:6:

```
Glu Val Gln Leu Gln Gln Ser Gly Pro Asp Leu Val Lys Pro Gly Ala
 1               5                  10                  15

Ser Val Lys Ile Ser Cys Lys Thr Ser Gly Tyr Thr Phe Thr Glu Tyr
            20                  25                  30

Thr Met His Trp Val Lys Gln Ser His Gly Arg Ser Leu Glu Trp Ile
        35                  40                  45

Gly Gly Ile Asn Pro Asn Asn Gly Asp Thr Ser Tyr Thr Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Thr Pro Tyr Tyr Ala Tyr Ala Ile Asp Ser Trp Gly Gln Gly Thr
                100                 105                 110

Ser Val Thr Val Ser Ser
            115
```

(2) INFORMATION FOR SEQ ID NO:7:

(i) SEQUENCE CHARACTERISTICS:
      (A) LENGTH: 333 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..333

(xi) SEQUENCE DESCRIPTION: SEQ ID NO:7:

```
GAC ATT GTG CTG ACC CAA TCT CCA GCT TCT TTG GCT GTG TCT CTA GGG          48
Asp Ile Val Leu Thr Gln Ser Pro Ala Ser Leu Ala Val Ser Leu Gly
 1               5                  10                  15

CAG AGG GCC ACC ATC TCC TGC AAG GCC AGC CAA AGT GTT GAT TAT GAT          96
Gln Arg Ala Thr Ile Ser Cys Lys Ala Ser Gln Ser Val Asp Tyr Asp
            20                  25                  30

GGT GAT AGT TAT ATG AAC TGG TAC CAA CAG AAA CCA GGA CAG CCA CCC         144
Gly Asp Ser Tyr Met Asn Trp Tyr Gln Gln Lys Pro Gly Gln Pro Pro
        35                  40                  45

AAA CTC CTC ATC TAT GCT GCA TCC AAT CTA GAA TCT GGG ATC CCA GCC         192
Lys Leu Leu Ile Tyr Ala Ala Ser Asn Leu Glu Ser Gly Ile Pro Ala
    50                  55                  60

AGG TTT AGT GGC AGT GGG TCT GGG ACA GAC TTC ACC CTC AAC ATC CAT         240
Arg Phe Ser Gly Ser Gly Ser Gly Thr Asp Phe Thr Leu Asn Ile His
65                  70                  75                  80

CCT GTG GAG GAG GAG GAT GGT GCA ACC TAT TAC TGT CAG CAA AGT AAT         288
Pro Val Glu Glu Glu Asp Gly Ala Thr Tyr Tyr Cys Gln Gln Ser Asn
                85                  90                  95
```

```
GAG GAT CCG TGG ACG TTC GGT GGA GGC ACC AAG CTG GAA ACT AAA                333
Glu Asp Pro Trp Thr Phe Gly Gly Gly Thr Lys Leu Glu Thr Lys
            100                 105                 110
```

( 2 ) INFORMATION FOR SEQ ID NO:8:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Gly Ala Thr Tyr Tyr Cys Gln Gln Ser Asn
                85                  90                  95

Glu Asp Pro Trp Thr Phe Gly Gly Gly Thr Lys Leu Glu Thr Lys
            100                 105                 110
```

( 2 ) INFORMATION FOR SEQ ID NO:9:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..357

( x i ) SEQUENCE DESCRIPTION: SEQ ID NO:9:

```
CAG GTG CAA CTA GTG CAG TCC GGC GCC GAA GTG AAG AAA CCC GGT GCT                 48
Gln Val Gln Leu Val Gln Ser Gly Ala Glu Val Lys Lys Pro Gly Ala
 1               5                  10                  15

TCC GTG AAG GTG AGC TGT AAA GCT AGC GGT TAT ACC TTC ACA AAA TAT                 96
Ser Val Lys Val Ser Cys Lys Ala Ser Gly Tyr Thr Phe Thr Lys Tyr
            20                  25                  30

GGA ATG AAC TGG GTT AGA CAG GCC CCA GGC CAA GGG CTC AAG TGG ATG                144
Gly Met Asn Trp Val Arg Gln Ala Pro Gly Gln Gly Leu Lys Trp Met
        35                  40                  45

GGC TGG AAA AAC ACC AAT ACT GGA GAG TCA ACA CAT GTT GAG GAG TTT                192
Gly Trp Lys Asn Thr Asn Thr Gly Glu Ser Thr His Val Glu Glu Phe
    50                  55                  60

AAG GGC AGG GTT ACC ATG TCC TTG GAC ACC TCT ACA AAC ACC GCC TAC                240
Lys Gly Arg Val Thr Met Ser Leu Asp Thr Ser Thr Asn Thr Ala Tyr
65                  70                  75                  80                85

ATG GAA CTG TCC AGC CTG CGC TCC GAG GAC ACT GCA GTT TAC TAC TGC                288
Met Glu Leu Ser Ser Leu Arg Ser Glu Asp Thr Ala Val Tyr Tyr Cys
                90                  95                  100

GCC AGA GAA TAT GAT TAC GAC GGG GGC TTC TCC TAT TGG GGA CAG GGT                336
```

```
Ala  Arg  Glu  Tyr  Asp  Tyr  Asp  Gly  Gly  Phe  Ser  Tyr  Trp  Gly  Gln  Gly
          105                      110                      115

ACC  CTT  GTC  ACC  GTC  AGT  TCA                                                    357
Thr  Leu  Val  Thr  Val  Ser  Ser
          120
```

( 2 ) INFORMATION FOR SEQ ID NO:10:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Gln  Val  Gln  Leu  Val  Gln  Ser  Gly  Ala  Glu  Val  Lys  Lys  Pro  Gly  Ala
 1                   5                    10                       15

Ser  Val  Lys  Val  Ser  Cys  Lys  Ala  Ser  Gly  Tyr  Thr  Phe  Thr  Lys  Tyr
               20                      25                        30

Gly  Met  Asn  Trp  Val  Arg  Gln  Ala  Pro  Gly  Gln  Gly  Leu  Lys  Trp  Met
          35                      40                       45

Gly  Trp  Lys  Asn  Thr  Asn  Thr  Gly  Glu  Ser  Thr  His  Val  Glu  Glu  Phe
     50                      55                       60

Lys  Gly  Arg  Val  Thr  Met  Ser  Leu  Asp  Thr  Ser  Thr  Asn  Thr  Ala  Tyr
 65                      70                       75                       80

Met  Glu  Leu  Ser  Ser  Leu  Arg  Ser  Glu  Asp  Thr  Ala  Val  Tyr  Tyr  Cys
                85                       90                       95

Ala  Arg  Glu  Tyr  Asp  Tyr  Asp  Gly  Gly  Phe  Ser  Tyr  Trp  Gly  Gln  Gly
               100                     105                      110

Thr  Leu  Val  Thr  Val  Ser  Ser
               115
```

( 2 ) INFORMATION FOR SEQ ID NO:11:

( i ) SEQUENCE CHARACTERISTICS:
        ( A ) LENGTH: 321 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..321

( x i ) SEQUENCE DESCRIPTION: SEQ ID NO:11:

```
GAC  ATC  CAG  ATG  ACC  CAG  AGC  CCA  AGC  AGC  CTG  AGC  GCC  AGC  GTG  GGT     48
Asp  Ile  Gln  Met  Thr  Gln  Ser  Pro  Ser  Ser  Leu  Ser  Ala  Ser  Val  Gly
 1                   5                    10                       15

GAC  AGA  GTG  ACC  ATC  ACC  TGT  AAA  GCC  AGC  CAG  GAT  GTG  GGT  GCT  GAT     96
Asp  Arg  Val  Thr  Ile  Thr  Cys  Lys  Ala  Ser  Gln  Asp  Val  Gly  Ala  Asp
               20                      25                       30

GTA  GCT  TGG  TAC  CAG  CAG  AAG  CCA  GGT  AAG  GCT  CCA  AAG  CTG  CTG  ATC    144
Val  Ala  Trp  Tyr  Gln  Gln  Lys  Pro  Gly  Lys  Ala  Pro  Lys  Leu  Leu  Ile
          35                      40                       45

TCC  TGG  GCA  TCC  ACC  CGG  CAC  ACT  GGT  GTG  CCA  AGC  AGA  TTC  AGC  GGT    192
Ser  Trp  Ala  Ser  Thr  Arg  His  Thr  Gly  Val  Pro  Ser  Arg  Phe  Ser  Gly
     50                      55                       60

AGC  GGT  AGC  GGT  ACC  GAC  TTC  ACC  TTC  ACC  ATC  AGC  AGC  CTC  CAG  CCA    240
Ser  Gly  Ser  Gly  Thr  Asp  Phe  Thr  Phe  Thr  Ile  Ser  Ser  Leu  Gln  Pro
 65                      70                       75                       80
```

| | | | | | | | | | | | | | | | | |
|---|---|---|---|---|---|---|---|---|---|---|---|---|---|---|---|---|
| GAG | GAC | ATC | GCC | ACA | TAC | TAC | TGC | CAA | CAA | TAT | AGC | AGC | TTT | CCA | CTC | 288 |
| Glu | Asp | Ile | Ala | Thr | Tyr | Tyr | Cys | Gln | Gln | Tyr | Ser | Ser | Phe | Pro | Leu | |
| | | | | 85 | | | | | 90 | | | | | 95 | | |
| ACG | TTC | GGC | CAA | GGG | ACC | AAG | GTG | GAA | ATC | AAA | | | | | | 321 |
| Thr | Phe | Gly | Gln | Gly | Thr | Lys | Val | Glu | Ile | Lys | | | | | | |
| | | | 100 | | | | | 105 | | | | | | | | |

( 2 ) INFORMATION FOR SEQ ID NO:12:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | | |
|---|---|---|---|---|---|---|---|---|---|---|---|---|---|---|---|
| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Lys | Ala | Ser | Gln | Asp | Val | Gly | Ala | Asp |
| | | | 20 | | | | | 25 | | | | | 30 | | |
| Val | Ala | Trp | Tyr | Gln | Gln | Lys | Pro | Gly | Lys | Ala | Pro | Lys | Leu | Leu | Ile |
| | | | 35 | | | | | 40 | | | | | 45 | | |
| Ser | Trp | Ala | Ser | Thr | Arg | His | Thr | Gly | Val | Pro | Ser | Arg | Phe | Ser | Gly |
| | 50 | | | | | 55 | | | | | 60 | | | | |
| Ser | Gly | Ser | Gly | Thr | Asp | Phe | Thr | Phe | Thr | Ile | Ser | Ser | Leu | Gln | Pro |
| 65 | | | | | 70 | | | | | 75 | | | | | 80 |
| Glu | Asp | Ile | Ala | Thr | Tyr | Tyr | Cys | Gln | Gln | Tyr | Ser | Ser | Phe | Pro | Leu |
| | | | | 85 | | | | | 90 | | | | | 95 | |
| Thr | Phe | Gly | Gln | Gly | Thr | Lys | Val | Glu | Ile | Lys | | | | | |
| | | | 100 | | | | | 105 | | | | | | | |

( 2 ) INFORMATION FOR SEQ ID NO:13:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..354

( x i ) SEQUENCE DESCRIPTION: SEQ ID NO:13:

| | | | | | | | | | | | | | | | | |
|---|---|---|---|---|---|---|---|---|---|---|---|---|---|---|---|---|
| CAG | GTG | CAA | CTA | GTG | CAG | TCC | GGC | GCC | GAA | GTG | AAG | AAA | CCC | GGT | GCT | 48 |
| Gln | Val | Gln | Leu | Val | Gln | Ser | Gly | Ala | Glu | Val | Lys | Lys | Pro | Gly | Ala | |
| 1 | | | | 5 | | | | | 10 | | | | | 15 | | |
| TCC | GTG | AAG | GTG | AGC | TGT | AAA | GCT | AGC | GGT | TAT | ACC | TTC | ACT | GAA | TAC | 96 |
| Ser | Val | Lys | Val | Ser | Cys | Lys | Ala | Ser | Gly | Tyr | Thr | Phe | Thr | Glu | Tyr | |
| | | | 20 | | | | | 25 | | | | | 30 | | | |
| ACC | ATG | CAT | TGG | GTT | AGA | CAG | GCC | CCA | GGC | CAA | GGG | CTC | GAG | TGG | ATT | 144 |
| Thr | Met | His | Trp | Val | Arg | Gln | Ala | Pro | Gly | Gln | Gly | Leu | Glu | Trp | Ile | |
| | | | 35 | | | | | 40 | | | | | 45 | | | |
| GGC | GGT | ATT | AAC | CCT | AAC | AAT | GGC | GAT | ACA | AGC | TAT | ACC | CAG | AAG | TTT | 192 |
| Gly | Gly | Ile | Asn | Pro | Asn | Asn | Gly | Asp | Thr | Ser | Tyr | Thr | Gln | Lys | Phe | |
| | | 50 | | | | | 55 | | | | | 60 | | | | |
| AAG | GGC | AAG | GCT | ACC | ATG | ACC | GTA | GAC | ACC | TCT | ACA | AAC | ACC | GCC | TAC | 240 |
| Lys | Gly | Lys | Ala | Thr | Met | Thr | Val | Asp | Thr | Ser | Thr | Asn | Thr | Ala | Tyr | |
| 65 | | | | | 70 | | | | | 75 | | | | | 80 | |
| ATG | GAA | CTG | TCC | AGC | CTG | CGC | TCC | GAG | GAC | ACT | GCA | GTT | TAC | TAC | TGC | 288 |
| Met | Glu | Leu | Ser | Ser | Leu | Arg | Ser | Glu | Asp | Thr | Ala | Val | Tyr | Tyr | Cys | |

|  |  |  |  |  |  |  |  |  |  |  |  |  |  |  |
|---|---|---|---|---|---|---|---|---|---|---|---|---|---|---|
|  |  |  | 85 |  |  |  |  | 90 |  |  |  |  | 95 |  |
| GCC | ACA | CCC | TAC | TAC | GCC | TAC | GCT | ATT | GAC | TCC | TGG | GGA | CAG | GGT | ACC | 336
| Ala | Thr | Pro | Tyr | Tyr | Ala | Tyr | Ala | Ile | Asp | Ser | Trp | Gly | Gln | Gly | Thr |
|  |  | 100 |  |  |  |  | 105 |  |  |  |  | 110 |  |  |

CTT GTC ACC GTC AGT TCA                                                                                354
Leu Val Thr Val Ser Ser
        115

( 2 ) INFORMATION FOR SEQ ID NO:14:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Ile
        35                  40                  45

Gly Gly Ile Asn Pro Asn Asn Gly Asp Thr Ser Tyr Thr Gln Lys Phe
    50                  55                  60

Lys Gly Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Tyr Tyr Ala Tyr Ala Ile Asp Ser Trp Gly Gln Gly Thr
            100                 105                 110

Leu Val Thr Val Ser Ser
        115

( 2 ) INFORMATION FOR SEQ ID NO:15:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..333

( x i ) SEQUENCE DESCRIPTION: SEQ ID NO:15:

GAC ATC CAG ATG ACC CAG AGC CCA AGC AGC CTG AGC GCC AGC GTG GGT      48
Asp Ile Gln Met Thr Gln Ser Pro Ser Ser Leu Ser Ala Ser Val Gly
 1               5                  10                  15

GAC AGA GTG ACC ATC ACC TGT AAG GCC AGC CAA AGT GTT GAT TAT GAT      96
Asp Arg Val Thr Ile Thr Cys Lys Ala Ser Gln Ser Val Asp Tyr Asp
            20                  25                  30

GGT GAT AGT TAT ATG AAC TGG TAC CAG CAG AAG CCA GGT AAG GCT CCA     144
Gly Asp Ser Tyr Met Asn Trp Tyr Gln Gln Lys Pro Gly Lys Ala Pro
        35                  40                  45

AAG CTG CTG ATC TAC GCT GCA TCC AAT CTA GAA TCT GGT GTG CCA AGC     192
Lys Leu Leu Ile Tyr Ala Ala Ser Asn Leu Glu Ser Gly Val Pro Ser
    50                  55                  60

AGA TTC AGC GGT AGC GGT AGC GGT ACC GAC TTC ACC TTC ACC ATC AGC     240

| | | | | | | | | | | | | | | | |
|---|---|---|---|---|---|---|---|---|---|---|---|---|---|---|---|
| Arg | Phe | Ser | Gly | Ser | Gly | Ser | Gly | Thr | Asp | Phe | Thr | Phe | Thr | Ile | Ser |
| 65 | | | | | 70 | | | | | 75 | | | | | 80 |

| | | | | | | | | | | | | | | | |
|---|---|---|---|---|---|---|---|---|---|---|---|---|---|---|---|
| AGC | CTC | CAG | CCA | GAG | GAC | ATC | GCC | ACC | TAC | TAC | TGC | CAG | CAA | AGT | AAT | 288
| Ser | Leu | Gln | Pro | Glu | Asp | Ile | Ala | Thr | Tyr | Tyr | Cys | Gln | Gln | Ser | Asn |
| | | | | 85 | | | | | 90 | | | | | 95 | |

| | | | | | | | | | | | | | |
|---|---|---|---|---|---|---|---|---|---|---|---|---|---|
| GAG | GAC | CCA | TGG | ACG | TTC | GGC | CAA | GGG | ACC | AAG | GTG | GAA | ATC | AAA | 333
| Glu | Asp | Pro | Trp | Thr | Phe | Gly | Gln | Gly | Thr | Lys | Val | Glu | Ile | Lys |
| | | | 100 | | | | | 105 | | | | | 110 | |

( 2 ) INFORMATION FOR SEQ ID NO:16:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Lys | Ala | Ser | Gln | Ser | Val | Asp | Tyr | Asp |
|---|---|---|---|---|---|---|---|---|---|---|---|---|---|---|---|
| | | | 20 | | | | | 25 | | | | | 30 | | |

| Gly | Asp | Ser | Tyr | Met | Asn | Trp | Tyr | Gln | Gln | Lys | Pro | Gly | Lys | Ala | Pro |
|---|---|---|---|---|---|---|---|---|---|---|---|---|---|---|---|
| | | 35 | | | | | 40 | | | | | 45 | | | |

| Lys | Leu | Leu | Ile | Tyr | Ala | Ala | Ser | Asn | Leu | Glu | Ser | Gly | Val | Pro | Ser |
|---|---|---|---|---|---|---|---|---|---|---|---|---|---|---|---|
| | 50 | | | | | 55 | | | | | 60 | | | | |

| Arg | Phe | Ser | Gly | Ser | Gly | Ser | Gly | Thr | Asp | Phe | Thr | Phe | Thr | Ile | Ser |
|---|---|---|---|---|---|---|---|---|---|---|---|---|---|---|---|
| 65 | | | | | 70 | | | | | 75 | | | | | 80 |

| Ser | Leu | Gln | Pro | Glu | Asp | Ile | Ala | Thr | Tyr | Tyr | Cys | Gln | Gln | Ser | Asn |
|---|---|---|---|---|---|---|---|---|---|---|---|---|---|---|---|
| | | | | 85 | | | | | 90 | | | | | 95 | |

| Glu | Asp | Pro | Trp | Thr | Phe | Gly | Gln | Gly | Thr | Lys | Val | Glu | Ile | Lys |
|---|---|---|---|---|---|---|---|---|---|---|---|---|---|---|
| | | | 100 | | | | | 105 | | | | | 110 | |

( 2 ) INFORMATION FOR SEQ ID NO:17:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

| Tyr | Asn | Lys | Arg | Lys | Arg | Ile | His | Ile | Gly | Pro | Gly | Arg | Ala | Phe | Tyr |
|---|---|---|---|---|---|---|---|---|---|---|---|---|---|---|---|
| 1 | | | | 5 | | | | | 10 | | | | | 15 | |

| Thr | Thr | Lys | Asn | Ile | Ile | Gly |
|---|---|---|---|---|---|---|
| | | | 20 | | | |

RECOMBINANT ANTI-HIV ANTIBODY AND PROCESS FOR PREPARING THE SAME

TECHNICAL FIELD OF THE INVENTION

The present invention relates to a novel recombinant anti-HIV antibody which can be expected to be used for treatment and prevention of AIDS provoked by human immunodeficiency virus (HIV). More specifically, the present invention relates to a recombinant anti-HIV antibody (reshaped antibody and chimeric antibody) having a neutralizing activity against HIV, said antibody being expressed using a genetic recombination technique from a mouse immunoglobulin gene and a human immunoglobulin gene, and a novel process for preparing the same. The present invention further relates to DNA fragments coding for H chain and L chain variable region which can be effectively used for expression of such useful recombinant antibody.

BACKGROUND ART

Acquired immunodeficiency syndrome (AIDS) is a viral disease caused by human immunodeficiency virus (HIV) belonging to a retrovirus. This disease, since discovery in the United States in 1981, has rapidly been spreading all over the world but an effective vaccine or a method for treating said disease has not yet been established.

Under such circumstances, there are reports on a relevance between the clinics and a neutralizing antibody in a group of thalassemic patients exhibiting HIV positive through transfusion and in a group of children with AIDS or ARC (AIDS related syndrome) [R. Guroff et al., J. Immunol., 138, p3731, (1987); R. Guroff et al., Pediatric Research, inpress]. It is mentioned in both reports that the clinical symptom was mild and benign in such cases where a neutralizing antibody was detectable, whereas it has become malignant in such cases where no neutralizing antibody could be detected. These facts suggest in vivo effectiveness of a neutralizing antibody. Therefore, an anti-HIV neutralizing antibody is expected to be usable for prevention of expansion of infection or for exclusion of infected cells, and to show a more enhanced effect when used in combination with anti-viral agents etc. now currently used clinically.

Though it is possible that the anti-HIV neutralizing antibody as mentioned above is directly obtained or prepared from patients with AIDS, this method is expected to bear a number of difficulties such as an ethical problem, availability of materials or a problem of biohazard. In this respect, as an alternative of such a high titer serum, the use of a monoclonal antibody having a neutralizing activity against HIV virus is considered. Although a basic technique for preparation of a monoclonal antibody has already been established in a mouse-type monoclonal antibody, a mouse antibody is hardly applicable to clinical applications in view of side effects (a mouse monoclonal antibody, when administered to humans, is considered to cause side effects such as anaphylactic shock or serum disease as a heterogeneous protein) etc., and hence, the use of a human monoclonal antibody is eventually preferable.

However, preparation of a human monoclonal antibody provokes many problems to be overcome for preparing an antibody having a desired specificity and is actually quite difficult in comparison to preparation of a mouse-type monoclonal antibody. For overcoming such problems, a method for preparing a chimeric monoclonal antibody utilizing a genetic recombination technique has recently been reported wherein the variable region, which characterizes the specificity of an antibody, has an amino acid sequence derived from a mouse antibody and the constant region has an amino acid sequence derived from a human antibody.

Such chimeric monoclonal antibody is obtained by expressing a mouse(V)-human(C) chimeric antibody gene, comprising a variable (V) gene as a material for V region which is cloned from a mouse hybridoma producing a mouse monoclonal antibody and a constant (C) gene as a material for C region which is cloned from a human cell such as a human antibody-producing cell, in an animal cell or a microorganism cell, etc., the desired chimeric monoclonal antibody being present in a culture supernatant. There have been several reports on a chimeric antibody [Japanese Patent First Publication No. 60-155132, Japanese Patent First Publication No. 61-47500] and the present inventors have already successfully prepared a chimeric antibody [Japanese Patent First Publication No. 2-2352]. Moreover, to further this idea of a chimeric antibody, preparation of a reshaped antibody has also been reported [Japanese Patent First Publication No. 62-296890].

Analysis of an immunoglobulin gene has made a rapid progress with a rapid advance of a genetic manipulation technique nowadays. It is well known that an immunoglobulin gene consists of a variable region (V region) gene involved in binding with an antigen and a constant region (C region) gene having a physiological activity concerned with interactions with complement or specific cells, etc. A V region gene is formed by each one gene selected from a group of a number of V gene fragments, a group of D gene fragments (not found in an L chain) and a group of J gene fragments, each selected genes being bound in this order. Furthermore, the bound gene fragment (V region gene) is further altered by a minute modification with a somatic mutation. That is, a specificity of an antibody is determined by a combination of each of gene fragments in V region gene of H chain and L chain and a somatic mutation [cf. Susumu Tonegawa, Nature, 302, p575 (1983); Tasuku Honjo, Annual Rev. Immunol. 1, p499 (1983)]. Accordingly, for a specific antigen, there deems to be both a combination of a specific VDJ gene fragment of H chain and a specific VJ gene fragment of L chain and a specific somatic mutation. In addition, a combination of these gene fragments or nucleotide or amino acid sequence thereof can hardly be deduced from a structure, nucleotide or amino acid sequence etc. of an antigen but can only be determined by isolating an antibody gene or an antibody protein from cells actually producing an antibody. In this way, a variable region of an antibody molecule has an amino acid sequence varying with every antigen determinant, and a variable region has an amino acid sequence which completely varies with every antigen.

As for a recombinant anti-HIV antibody aimed by the present invention, the present inventors have already published 0.5β recombinant antibody as an anti-HIV neutralizing antibody [Japanese Patent First Publication No. 2-2352], but said recombinant antibody can specifically neutralize HTLV-IIIB but not HTLV-IIIMN which is epidemically prevalent. As mentioned above, for preparation of a recombinant antibody, it is very important to find out a gene coding for an amino acid sequence of a variable region of an antibody molecule having a binding capacity with a desired antigen. Because of difficulty of finding a gene coding for an amino acid sequence of a variable region of an antibody having a neutralizing activity against HIV, especially HTLV-IIIMN, aimed by the present invention, there is no report of obtention of a recombinant antibody which binds with and substantially neutralizes HTLV-IIIMN.

OBJECT OF THE INVENTION

Under such circumstances, the present inventors have successfully isolated a gene coding for a variable region of a monoclonal antibody having a neutralizing activity against HIV (HTLV-IIIMN) from cells (hybridomas) producing said antibody. The present inventors have further attempted to make an expression of a mouse-human recombinant antibody using said gene, and as a result, have successfully prepared a recombinant antibody having a neutralizing activity against HIV (HTLV-IIIMN), and thus the present invention has been completed. That is, the present invention provides for a gene coding for a variable region of an anti-HIV neutralizing antibody which has hitherto never been reported, and provides for a recombinant anti-HIV antibody expressed in a transformed cell by using said gene. An object of the present invention is to make it possible to develop diagnosing, treating and preventing agents for AIDS with decreased side effects comprising said novel anti-HIV recombinant antibody.

BRIEF EXPLANATION OF DRAWINGS

FIG. 1 shows a nucleotide sequence (SEQ ID NO:1) of a DNA fragment of the present invention coding for H chain variable region of anti-HIV neutralizing antibody μ39.1 shown in Example (3) and an amino acid sequence (SEQ ID NO:2) deduced therefrom.

FIG. 2 shows a nucleotide sequence (SEQ ID NO:3) of a DNA fragment of the present invention coding for L chain variable region of anti-HIV neutralizing antibody μ39.1 shown in Example (3) and an amino acid sequence (SEQ ID NO:4) deduced therefrom.

FIG. 3 shows a nucleotide sequence (SEQ ID NO:5) of a DNA fragment of the present invention coding for H chain variable region of anti-HIV neutralizing antibody μ5.5 shown in Example (3) and an amino acid sequence (SEQ ID NO:6) deduced therefrom.

FIG. 4 shows a nucleotide sequence (SEQ ID NO:7) of a DNA fragment of the present invention coding for L chain variable region of anti-HIV neutralizing antibody μ5.5 shown in Example (3) and an amino acid sequence (SEQ ID NO:8) deduced therefrom.

FIG. 9 shows a nucleotide sequence (SEQ ID NO:9) of a DNA fragment coding for an H chain variable region of anti-HIV reshaped antibody μ39.1 prepared in Example (6) and an amino acid sequence deduced therefrom (the underlined sequence shows an amino acid sequence (SEQ ID NO:10) derived from a mouse antibody).

FIG. 10 shows a nucleotide sequence (SEQ ID NO:11) of a DNA fragment coding for an L chain variable region of anti-HIV reshaped antibody μ39.1 prepared in Example (6) and an amino acid sequence deduced therefrom (the underlined sequence shows an amino acid sequence (SEQ ID NO:12) derived from a mouse antibody).

FIG. 11 shows a nucleotide sequence (SEQ ID NO:13) of a DNA fragment coding for an H chain variable region of anti-HIV reshaped antibody μ5.5 prepared in Example (6) and an amino acid sequence deduced therefrom (the underlined sequence shows an amino acid sequence (SEQ ID NO:14) derived from a mouse antibody).

FIG. 12 shows a nucleotide sequence (SEQ ID NO:15) of a DNA fragment coding for an L chain variable region of anti-HIV reshaped antibody μ5.5 prepared in Example (6) and an amino acid sequence deduced therefrom (the underlined sequence shows an amino acid sequence (SEQ ID NO:16) derived from a mouse antibody).

DISCLOSURE OF THE INVENTION

Figure 5:
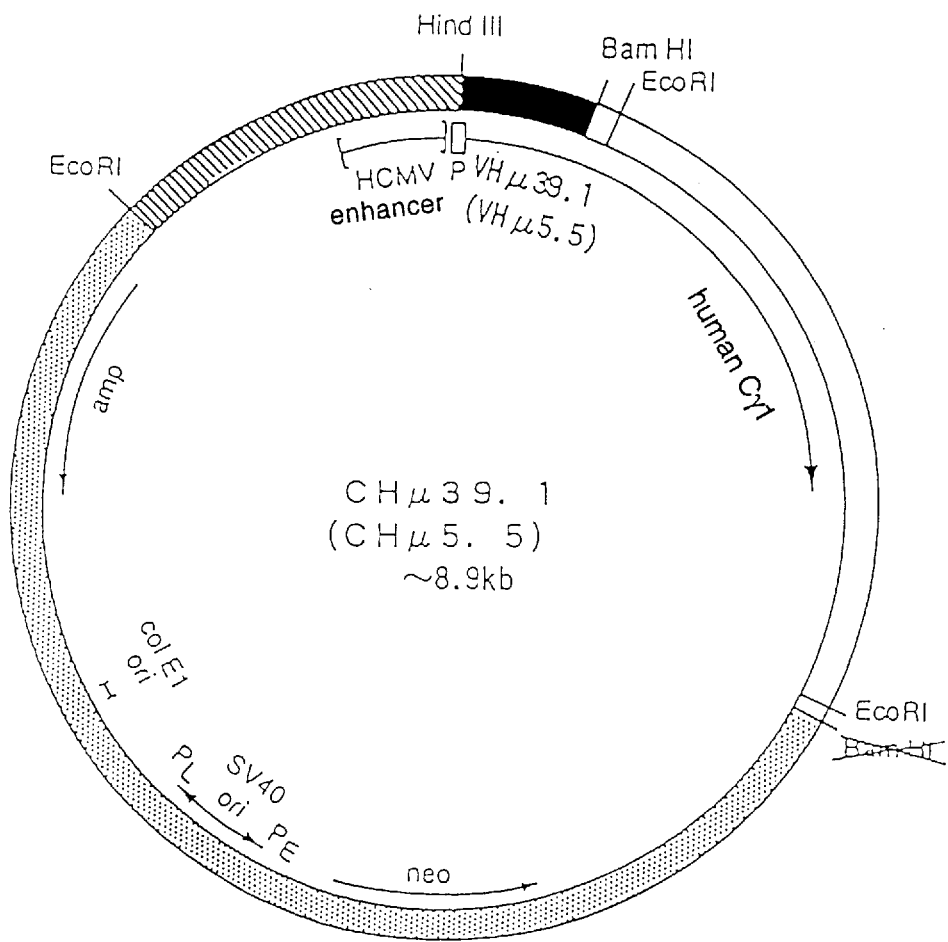
FIG. 5 shows a structure of anti-HIV chimeric antibody H chain expression plasmids, CHμ39.1 and CHμ5.5, constructed in Example (4).

Cells producing anti-HIV (HTLV-IIIMN) mouse monoclonal antibody used in the present invention are prepared by the hitherto established technique for preparing a mouse monoclonal antibody. For example, it can be prepared by immunizing mice with an appropriate immunogen, e.g. a viral particle obtained from HIV (HTLV-IIIMN) producing cells, or a purified envelope glycoprotein gp120, or a recombinant peptide prepared by using a genetic recombination technique, preferably a recombinant peptide corresponding to gp120 amino acid sequence Nos. 247–370, or a suitable synthetic peptide prepared based on an amino acid sequence of said viral protein, preferably a synthetic peptide corresponding to gp120 amino acid sequence Nos. 303–325, etc., fusing the obtained spleen cells with mouse myeloma cells, selecting from the obtained hybridomas the cells which react with a purified envelope glycoprotein gp120 or the above recombinant peptide or the above synthetic peptide, and culturing said cells. Further, from the thus obtained anti-HIV mouse monoclonal antibody producing cells, the cells producing a monoclonal antibody having a neutralizing activity against HIV are selected. In case of HIV, it is not easy to obtain a monoclonal antibody having such neutralizing activity due to characteristics of its own, but as such a cell line, the present inventors have already successfully established hybridomas μ39.1 and μ5.5 cells which produce an antibody having a neutralizing activity against HIV (HTLV-IIIMN) [Japanese Patent Application No. 2-188300], these cell lines being most preferably used for the present invention.

The gene fragment coding for a variable region of the present invention is isolated from the above-mentioned anti-HIV neutralizing monoclonal antibody producing cells and a gene sequence thereof is analyzed. However, as mentioned above, such cells contains a large number of genes consisting of V region in addition to a gene coding for a V region specific for a desired anti-HIV antibody (For example, a group of V gene alone of VH chain which determines a specificity of a mouse antibody includes more than 100 different genes, a group of D gene includes more than 11 genes, and a group of J gene includes 4 genes. Similarly, a group of V gene of Vκ chain includes more than about 300 genes, and a group of J gene includes 4 genes), and hence, it is necessary to isolate a gene coding for a V region specific for a desired anti-HIV antibody. A V region gene can be isolated by the conventional gene manipulation technique, including, for example, a method of cloning a V region gene from a chromosomal DNA of the cell by using the conventional method [cf. for example, T. Maniatis "Molecular Cloning" Cold Spring Harbor Lab. (1982)] or a method of synthesizing cDNA from mRNA of the cells using the conventional method [e.g. D. M. Glover ed. "DNA cloning Vol. I" IRL press (1985)] and cloning the V region gene. In either method, there can be utilized, as a probe for cloning a V region gene, a DNA probe etc. synthesized by referring to the nucleotide sequence of a mouse immunoglobulin gene which has already been reported [e.g. Sakano et al., Nature, 286, p676, (1980); E. E. Max et al., J. Biol. Chem., 256, p5116, (1981)]. Cloning with PCR (polymerase chain reaction) can also be conducted [R. Orlandi, et al., Proc. Natl. Acad. Sci. USA, 86, 3833 (1989); W. D. Huse, et al., Science, 246, 1275 (1989)].

The thus cloned V region gene was genetically analyzed by various methods such as a method for preparing a chimeric antibody [Japanese Patent First Publication No. 2-2352] or a method for preparing a reshaped antibody [Japanese Patent First Publication No. 62-296890]. As a result, it was found that the gene fragment of the present invention coding for an anti-HIV antibody V region is characterized by that it contains, as a specific gene sequence, a gene coding for an amino acid of (H-a):

(a) Lys-Tyr-Gly-Met-Asn (Amino Acids 31–35 of SEQ ID NO:2)
(b) Trp-Lys-Asn-Thr-Asn-Thr-Gly-Glu-Ser-Thr-His-Val-Glu-Glu-Phe-Lys-Gly (Amino Acids 50–66 of SEQ ID NO:2)
(c) Glu-Tyr-Asp-Tyr-Asp-Gly-Gly-Phe-Ser-Tyr (Amino Acids 99–108 of SEQ ID NO:2)

or (H-b):
(a) Glu-Tyr-Thr-Met-His (Amino Acids 31–35 of SEQ ID NO:6)
(b) Gly-Ile-Asn-Pro-Asn-Asn-Gly-Asp-Thr-Ser-Tyr-Thr-Gln-Lys-Phe-Lys-Gly (Amino Acids 50–66 of SEQ ID NO:6)
(c) Pro-Tyr-Tyr-Ala-Tyr-Ala-Ile-Asp-Ser (Amino Acids 99–107 of SEQ ID NO:6)

within a gene coding for H chain as a part, and a gene sequence coding for an amino acid of (L-a):
(a) Lys-Ala-Ser-Gln-Asp-Val-Gly-Ala-Asp-Val-Ala (Amino Acids 24–34 of SEQ ID NO:4)
(b) Trp-Ala-Ser-Thr-Arg-His-Thr (Amino Acids 50–56 of SEQ ID NO:4)
(c) Gln-Gln-Tyr-Ser-Ser-Phe-Pro-Leu-Thr (Amino Acids 89–97 of SEQ ID NO:4)

or (L-b):
(a) Lys-Ala-Ser-Gln-Ser-Val-Asp-Tyr-Asp-Gly-Asp-Ser-Tyr-Met-Asn (Amino Acids 24–38 of SEQ ID NO:8)
(b) Ala-Ala-Ser-Asn-Leu-Glu-Ser (Amino Acids 54–60 of SEQ ID NO:8)
(c) Gln-Gln-Ser-Asn-Glu-Asp-Pro-Trp-Thr (Amino Acids 93–101 of SEQ ID NO:8)

within a gene coding for L chain as a part. Each set of these three amino acid sequences contained in H chain and L chain, respectively, are considered to be an important amino acid sequence which determines a binding capacity of an antibody molecule and such amino acid sequences were considered to be closely related to a function of an antibody molecule having a neutralizing activity against HIV. That is, by referring to the results of general analysis of an antibody gene reported by Kabat et al. [Sequences of Proteins of Immunological Interest, 4th. ed. U.S. Department of Health and Human Services (1987)], the above amino acid sequences were found to be a sequence of complementarity determining regions (CDR1 to CDR3) in a variable region which determines an antibody activity of the anti-HIV antibody of the present invention. A gene coding for such variable region of an antibody molecule having an anti-HIV neutralizing activity includes, by way of a preferable example, gene fragments coding for the amino acid sequences as shown in FIG. 1 or FIG. 3 or for the amino acid sequences as shown in FIG. 2 or FIG. 4 for H chain or L chain, respectively. A specific nucleotide sequence of such genes includes, for example, the nucleotide sequences as shown in FIG. 1 or FIG. 3, or FIG. 2 or FIG. 4, for H chain or L chain, respectively.

Based on the above nucleotide sequences provided by the present invention, a recombinant antibody having a neutralizing activity against HIV can be prepared. That is, a desired recombinant anti-HIV antibody, i.e. anti-HIV chimeric antibody or anti-HIV reshaped antibody, can be prepared by preparing, as a gene coding for a variable region of such recombinant antibody, synthetic DNAs etc. which are DNA fragments coding for the above amino acid sequences as a complementarity determining region, and fusing said DNAs with a gene coding for a human immunoglobulin. The thus prepared recombinant anti-HIV antibody of the present invention is characterized by that it contains, as a complementarity determining region of H chain variable region, the following sequences (CDR1 to CDR3):

(H-A)
CDR1: Lys-Tyr-Gly-Met-Asn (Amino Acids 31–35 of SEQ ID NO:10)
CDR2: Trp-Lys-Asn-Thr-Asn-Thr-Gly-Glu-Ser-Thr-His-Val-Glu-Glu-Phe-Lys-Gly (Amino Acids 50–66 of SEQ ID NO:10)
CDR3: Glu-Tyr-Asp-Tyr-Asp-Gly-Gly-Phe-Ser-Tyr (Amino Acids 99–108 of SEQ ID NO:10) or (H-B)
CDR1: Glu-Tyr-Thr-Met-His (Amino Acids 31–35 of SEQ ID NO:14)
CDR2: Gly-Ile-Asn-Pro-Asn-Asn-Gly-Asp-Thr-Ser-Tyr-Thr-Gln-Lys-Phe-Lys-Gly (Amino Acids 50–66 of SEQ ID NO:14)
CDR3: Pro-Tyr-Tyr-Ala-Tyr-Ala-Ile-Asp-Ser (Amino Acids 99–106 of SEQ ID NO:14).

The recombinant anti-HIV antibody of the present invention is also characterized by that it contains, as a complementarity determining region of L chain variable region, the following sequences (CDR1 to CDR3):

(L-A)
CDR1: Lys-Ala-Ser-Gln-Asp-Val-Gly-Ala-Asp-Val-Ala (Amino Acids 24–34 of SEQ ID NO:12)
CDR2: Trp-Ala-Ser-Thr-Arg-His-Thr (Amino Acids 50–56 of SEQ ID NO:12)
CDR3: Gln-Gln-Tyr-Ser-Ser-Phe-Pro-Leu-Thr or (L-B):
CDR1: Lys-Ala-Ser-Gln-Ser-Val-Asp-Tyr-Asp-Gly-Asp-Ser-Tyr-Met-Asn (Amino Acids 24–38 of SEQ ID NO:16)
CDR2: Ala-Ala-Ser-Asn-Leu-Glu-Ser (Amino Acids 54–60 of SEQ ID NO:16)
CDR3: Gln-Gln-Ser-Asn-Glu-Asp-Pro-Trp-Thr (Amino Acids 93–101 of SEQ ID NO:16).

Furthermore, the present inventors have also found that, in preparing a reshaped antibody, a recombinant antibody which more fully retains an original antibody activity can be obtained by replacing, in addition to complementarity determining regions, a portion of frame (FR) region adjacent to said complementarity determining regions with a mouse-derived sequence rather than by replacing the complementarity determining regions alone with a mouse-derived sequence as hitherto reported.

That is, when the above complementarity determining region sequences (H-A) are used as an H chain variable region gene, an anti-HIV reshaped antibody having a more excellent activity can be prepared by preparing an H chain variable region gene wherein one amino acid at the C terminus of FR1 adjacent to the complementarity determining region CDR1 in a variable region is threonine (Thr), a four amino acid sequence at the C terminus of FR2 adjacent to CDR2 is Lys-Trp-Met-Gly (Amino Acids 46–49 of SEQ ID NO:10), a five amino acid sequence at the N terminus of FR3 adjacent to CDR2 is Arg-Val-Thr-Met-Ser (Amino Acids 67–71 of SEQ ID NO:10) and one amino acid at the C terminus of FR3 adjacent to CDR3 is arginine (Arg). Similarly, when the above complementarity determining region sequences (H-B) are used as an H chain variable region gene, an anti-HIV reshaped antibody having a more excellent activity can be prepared by preparing an H chain variable region gene wherein one amino acid at the C terminus of FR1 adjacent to the complementarity determining region CDR1 in a variable region is threonine (Thr), a two amino acid sequence at the C terminus of FR2 adjacent to CDR2 is Ile-Gly (Amino Acids 48–49 of SEQ ID NO:14), a six amino acid sequence at the N terminus of FR3 adjacent to CDR2 is Lys-Ala-Thr-Met-Thr-Val (Amino Acids 67–72 of SEQ ID NO:14) and one amino acid at the C terminus of FR3 adjacent to CDR3 is threonine (Thr). When the above complementarity determining region sequences (L-A) are used as an L chain variable region gene, it is preferable to prepare an L chain variable region gene wherein one amino acid at the C terminus of FR2 adjacent to the complementarity determining region CDR2 in a variable region is serine (Ser).

A nucleotide sequence of the thus prepared gene coding for an H chain variable region of the anti-HIV reshaped antibody of the present invention, and an amino acid sequence deduced therefrom, includes, as a preferable example, the sequences as shown in FIG. 9 or FIG. 11 (wherein the underlined portion shows an amino acid sequence derived from mice). On the other hand, a nucleotide sequence of the gene coding for an L chain variable region of the anti-HIV reshaped antibody of the present invention, and an amino acid sequence deduced therefrom, includes, as a preferable example, the sequences as shown in FIG. 10 or FIG. 12 (wherein the underlined portion shows an amino acid sequence derived from mice).

On the other hand, in preparing an anti-HIV chimeric antibody in accordance with the present invention, a nucleotide sequence of the gene coding for an H chain variable region and an amino acid sequence deduced therefrom includes, as a preferable example, the sequences as shown in FIG. 1 or FIG. 3. A nucleotide sequence of the gene coding for an L chain variable region and an amino acid sequence deduced therefrom includes, as a preferable example, the sequences as shown in FIG. 2 or FIG. 4.

On the other hand, a constant (C) region gene of a human immunoglobulin H chain gene and L chain gene used for preparing the anti-HIV recombinant antibody can be isolated in the same manner, for example, from a human antibody producing cell. Since rearrangement does not occur in a C region gene, a human antibody producing cell is not necessarily used for isolating a human C region gene. The isolation can be conducted in the same way as in the isolation of the mouse V region gene as mentioned above. A C region gene is not limited to γ1 chain or κ chain but any kind of C region gene such as μ chain, α chain, γ2 chain, γ3 chain, γ4 chain, ε chain, or λ chain can be used. However, if a complement activating capacity or an antibody-dependent cellular cytotoxicity is desired, γ1 chain is preferable.

The anti-HIV recombinant antibody gene, both an H chain gene and an L chain gene, can be constructed basically by combining the above-mentioned two gene fragments (V region gene and C region gene). For example, the construction can be carried out in accordance with the method previously shown by Watanabe et al. [Watanabe et al., Cancer Research, 47, p999–1005, (1987)], or methods outlined by M. Bruggemann [Waldmann H (ed) Monoclonal Antibody Therapy. Prog Allergy. Basel, Karger, 1988, vol 45, pp91] or by S. L. Morrison [Advances in Immunology, 44, 65, (1989)]. A vector system varies depending on a host used for expression such as an animal cell expression system, an E. coli expression system, or an yeast expression system, but the gene of the present invention can be expressed in any of these expression systems. In addition, a gene amplification system such as DHFR may also be used.

The thus prepared recombinant antibody of the present invention was confirmed to have a neutralizing activity against HIV, and hence, the present invention allows for preparation of an anti-HIV recombinant antibody which hitherto has never been prepared. Such anti-HIV recombinant antibody, in the clinic of AIDS, can be a substantially effective treating agent for AIDS. Furthermore, the gene fragments coding for the anti-HIV antibody variable region provided by the present invention disclose a specific amino acid sequence or nucleotide sequence of a variable region of an antibody having a neutralizing activity against HIV and allows for development of a more excellent anti-HIV recombinant antibody molecule through modification or partial replacement of a desired antibody molecule by employing a further advanced genetic recombination technique.

BEST MODE FOR CARRYING OUT THE INVENTION

The present invention is explained in more detail by Examples but it should not be construed to be limited thereto.

EXAMPLE (1) Preparation of anti-HIV mouse monoclonal antibody producing cells A method for preparing a hybridoma producing an anti-HIV mouse monoclonal antibody is shown hereinbelow. An antigen for immunization included a synthetic peptide corresponding to an amino acid sequence Nos. 303 to 325 of HTLV-IIIMN strain envelope glycoprotein gp120 (SP-1: Tyr-Asn-Lys-Arg-Lys-Arg-Ile-His-Ile-Gly-Pro-Gly-Arg-Ala-Phe-Tyr-Thr-Thr-Lys-Asn-Ile-Ile-Gly (SEQ.ID.NO:17)) and a peptide-KLH (keyhole limpet hemocyanin) conjugate comprising said synthetic peptide bound to KLH, or a viral particle obtained from a culture supernatant of HTLV-IIIMN producing cells (H9/HTLV-IIIMN) by sucrose density-gradient centrifugation, or gp120 obtained by lysing cells from H9/HTLV-IIIMN culture with 1% TritonX-100 and then purifying by affinity chromatography through ConA-Sepharose 4B column and HIV antibody (IgG)-Sepharose 4B column, or HTLV-IIIMN gp120 V3 domain (amino acid 247–370) β-galactosidase fused protein which is prepared by isolating and amplifying by PCR method [G. I. LaRosa et al., Science Vol. 249 p932 (1990)] a DNA fragment coding for HTLV-IIIMN gp120 V3 domain (amino acid 247–370) from a high molecular weight DNA (genomic DNA) of H9/HTLV-IIIMN cells and expressing said DNA fragment in E. coli using pUEX2 (manufactured by Amersham) expression vector, or a combination of these antigens. After immunization of BALB/c mice 4 times with these immunogens, spleen cells were taken out and cell-fused with P3X63Ag8-U1X63 mouse myeloma cells [ATCC CRL 1597] using polyethylene glycol (Sigma) and cloning was conducted. A binding activity to the above immunogens of antibodies in the culture supernatant of the obtained clones was measured by enzyme immunoassay. For the clones deemed to be positive, the results were further confirmed by a Western blotting method and an indirect fluorescence method to establish hybridomas producing anti-HIV monoclonal antibodies, μ39.1 or μ5.5 [Japanese Patent Application No. 2-188300, deposit number; μ39.1 (Ferm P-11472), μ5.5 (FERM BP-3402), deposited with Fermentation Research Institute Agency of Industrial Science and Technology, 1–3, Higashi 1-chome, Tsukuba-shi, Ibaraki-ken, 305, Japan]. These antibodies bind to SP-1 peptide and inhibit syncytium formation between HIV-infected cells and uninfected CD4 positive cells. Furthermore, a neutralizing activity of these antibodies was also confirmed in a viral neutralization test where these antibodies are mixed with HIV virus and cells (H9) are infected with this mixture.

For preparing a V region gene of the anti-HIV recombinant antibody of the present invention as mentioned hereinbelow, the cells producing these anti-HIV mouse monoclonal antibodies having said neutralizing activity (μ39.1, μ5.5 cells) were used.

(2) Isolation of anti-HIV antibody mouse V region gene

The isolation of a mouse immunoglobulin variable (V) region gene was carried out in the following manner.

A whole RNAs were extracted from μ39.1 and μ5.5 cells in accordance with the conventional method [D. M. Glover ed. "DNA cloning Vol. I" IRL press (1985)] and a single-stranded cDNA was synthesized using a cDNA synthesizer System Plus (Amersham). Using this single-stranded cDNA as a template, a polymerase chain reaction (PCR) was conducted using DNA primers which were synthesized based on the nucleotide sequences of V region and J region as classified by Kabat et al. [Sequences of Proteins of Immunological Interest 4th ed., Public Health Service, NIH, Washington DC, 1987]. A HindIII site and a BamHI site were introduced into the V region primer and the J region primer, respectively. PCR was conducted in accordance with the protocol of CETUS. That is, each 100 pmol of these primers were employed and reagents for PCR were those in a kit manufactured by CETUS. PCR was conducted by 25 cycles, each cycle comprising 94° C. for 1 minute, 55° C. for 1 minute and 72° C. for 1 minute. After PCR, the obtained DNA fragments were cloned into the HincII site of pUC18 (manufactured by Takara Shuzo; the reagents used in Examples were those manufactured by Takara Shuzo or Toyobo unless otherwise mentioned).

(3) Nucleotide sequence of anti-HIV antibody mouse V region gene

Using Sequenase Ver. 2 kit manufactured by Toyobo, the V region gene incorporated into pUC18 was sequenced. The nucleotide sequences of μ39.1 and μ5.5 obtained thereby are shown in FIGS. 1 to 4. The amino acid sequences deduced from the nucleotide sequences are also shown in FIGS. 1 to 4. Both nucleotide sequences of μ39.1 and μ5.5 exhibited rearrangement specific for the V region gene and showed an open reading frame (ORF) which allows for expression.

(4) Preparation of anti-HIV chimeric antibody

Figure 6:
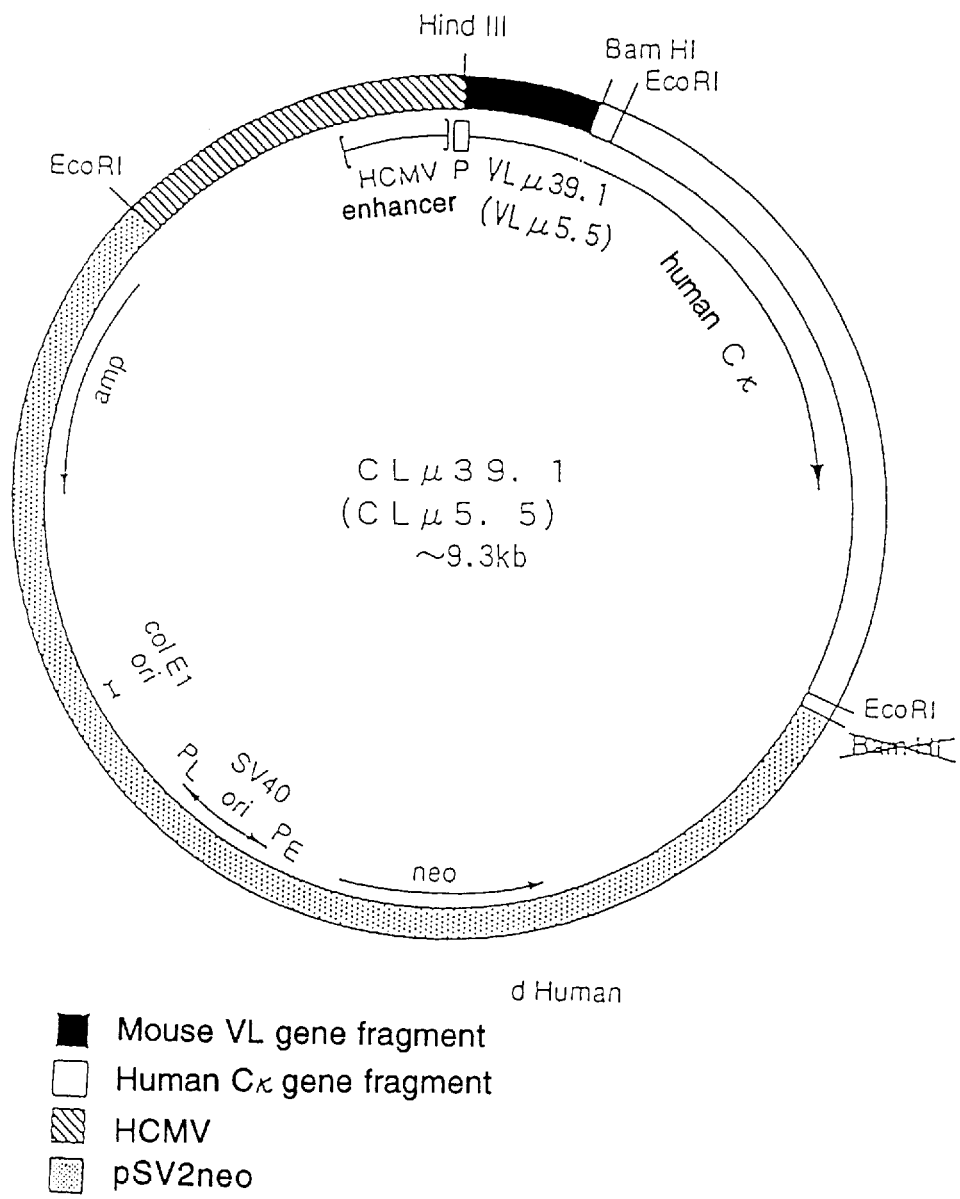
FIG. 6 shows a structure of anti-HIV chimeric antibody L chain expression plasmids, CLμ39.1 and CLμ5.5, constructed in Example (4).

In order to confirm that the V region genes μ39.1 and μ5.5 isolated in the above (2) are actually a gene coding for a V region responsible for an anti-HIV activity, a mouse-human chimeric antibody was prepared. For expression of a chimeric antibody, expression vectors HCMV-κ and HCMV-γ1 carrying enhancer and promoter of human cytomegalovirus (HCMV) [N. Whittle, et al., Protein Engineering, 1, 499 (1987)] were used, respectively. HCMV-κ contains a human κ chain constant region gene and HCMV-γ1 contains a human γ1 chain constant region gene. The μ39.1 V region gene prepared in the above procedure (2) was digested with restriction enzymes HindIII and BamHI and the VH and VL fragments were incorporated into the HindIII-BamHI site of HCMV-γ1 and HCMV-κ, respectively. FIGS. 5 and 6 show a structure of μ39.1 chimeric antibody gene expression vectors (CHμ39.1 and CLμ39.1, respectively). Similarly, the μ5.5 VH and VL region genes were incorporated into HCMV-γ1 and HCMV-κ (CHμ5.5 and CLμ5.5, respectively; cf. FIGS. 5 and 6).

(5) Expression of anti-HIV chimeric antibody

Figure 7:
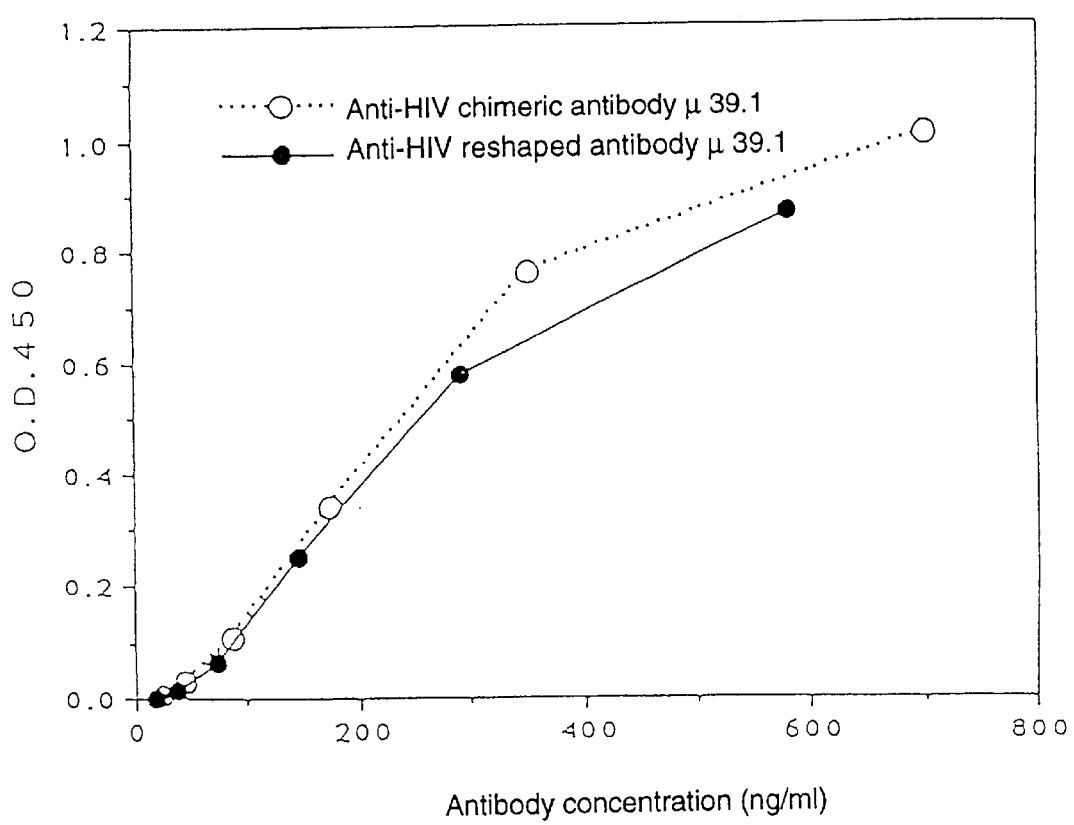
FIG. 7 shows anti-HIV activities of anti-HIV chimeric antibody μ39.1 measured in Example (5) and of anti-HIV reshaped antibody μ39.1 measured in Example (7).

An activity of an antibody shown by the μ39.1 or μ5.5 chimeric antibody gene constructed as mentioned above was examined in a transient expression system using COS7 cells [ATCC CRL 1651]. Using an Electroporation device manufactured by Bio-Rad, a mixture of CHμ39.1 and CLμ39.1 plasmid DNAs or a mixture of CHμ5.5 and CLμ5.5 plasmid DNAs were introduced into COS7 cells in accordance with the protocol of Boi-Rad and the cells were cultured in DMEM culture medium supplemented with 10% fetal calf serum (GIBCO). After three days, a culture supernatant was collected and an activity of antibodies present in the culture supernatant was measured by ELISA employing an anti-human IgG or SP-1 antigen peptide. As a result, as shown in FIG. 7, both expression products from a mixture of CHμ39.1 and CLμ39.1 plasmid DNAs and from a mixture of CHμ5.5 and CLμ5.5 plasmid DNAs bound to SP-1 peptide. Accordingly, it was confirmed that the μ39.1 and μ5.5 V region genes isolated in the procedure (2) are actually a gene coding for a V region of an antibody having an anti-HIV activity.

(6) Preparation of anti-HIV reshaped antibody

Figure 8:
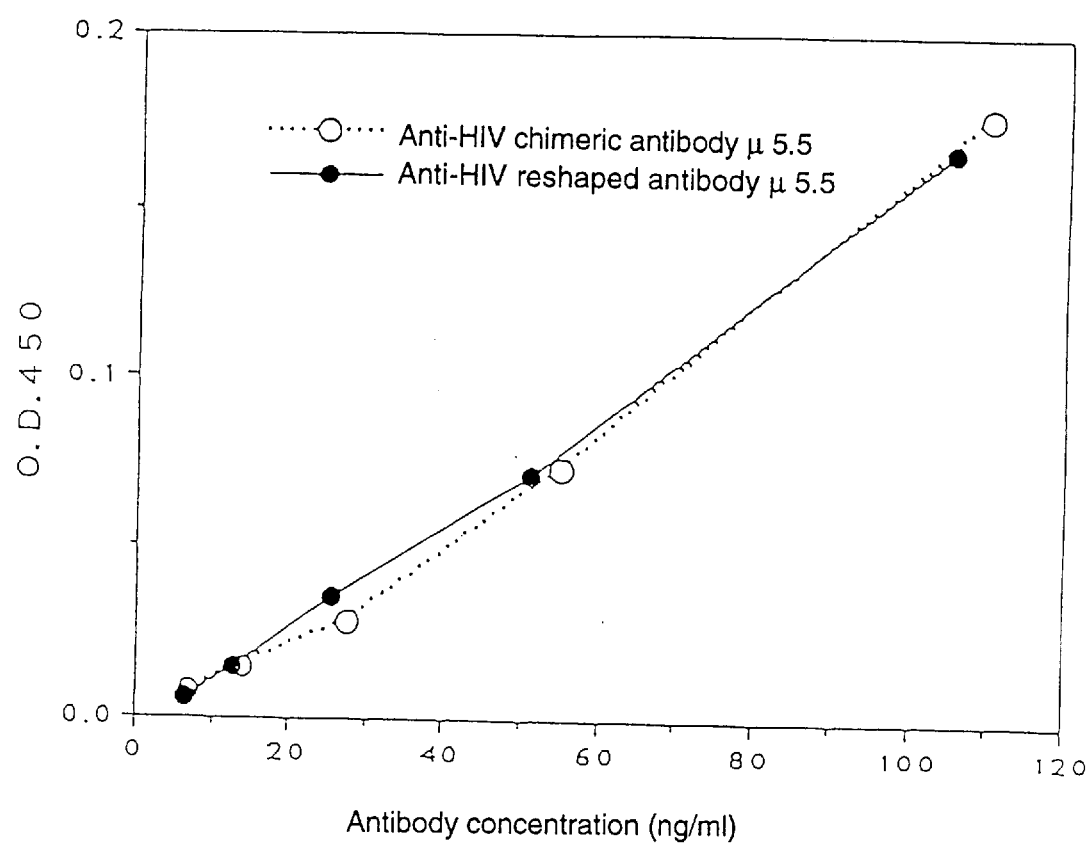
FIG. 8 shows anti-HIV activities of anti-HIV chimeric antibody μ5.5 measured in Example (5) and of anti-HIV reshaped antibody μ5.5 measured in Example (7).

In order to study which portion of the VH or VL region of the cloned μ39.1 or μ5.5 is important for binding to an antigen, CDR (complementarity determining) regions of μ39.1 and μ5.5 were transplanted into human V regions. This was carried out in accordance with the method for preparing a reshaped antibody [Japanese Patent First Publication No. 62-296890]. CDR regions of VH region of μ39.1 and μ5.5 were transplanted into VH region having a framework (FR) region of human subgroup I [SGI: donated by Dr. Bendig in MRC Collabrative Center, England](FIGS. 8 and 10) whereas CDR regions of VL region of μ39.1 and μ5.5 were transplanted into VL region having an FR region of human κ chain [REI: W. Palm and N. Hilscmann Z. Physiol. Chem., 356, 167 (1975)](FIGS. 9 and 11). Specifically, a reshaped antibody was prepared by an Amersham-PCR method which combines a kit from Amersham (Oligonucleotide-directed in vitoro mutagenesis system version 2 code RPN. 1523) with PCR [Saiki, R. G. et al., Science, 239, 487 (1988)]. A long chain nucleotide coding for the portion to be transplanted of VH or VL region of μ39.1 or μ5.5 was annealed to M13 DNA in which the V region gene of SGI or REI was incorporated, and then an elongation and binding of DNA was conducted in a solution containing dCTPαS. The template M13 DNA was cleaved with NciI and the template DNA was digested with Exonuclease III to give only the mutated M13 DNA (up to this procedure was conducted in accordance with the protocol of Amersham). Then, using the product after Exonuclease III digestion as a template, PCR was carried out using a universal primer (UP: this primer contains a sequence complementary to the 5' site of M13mp18) and a reverse primer (RSP: this primer contains the same sequence as the 3' site of M13mp18). Each 20 pmol of these primers was employed and the reagents for PCR were those from CETUS. PCR was conducted by 25 cycles, each cycle comprising 94° C. for 1 minute, 55° C. for 1 minute and 74° C. for 1 minute. After completion of PCR, the products were digested with BamHI/HindIII and the digested products were incorporated into the BamHI-HindIII site of pUC18, which was used for transformation of DH5α (BRL). As a primary screening, a colony hybridization was conducted using the CDR primers employed in the mutagenesis in accordance with the protocol of the Amersham kit to select clones with successful mutagenesis in CDR. Then, as a secondary screening, a plasmid was prepared from the clones obtained in the primary screening and a sequencing was carried out with a Sequenase kit (Toyobo) to confirm a correct CDR transplantion. In this way, reshaped V regions of μ39.1 or μ5.5 (RHμ39.1, RLμ39.1, RHμ5.5, RLμ5.5, respectively: cf. FIGS. 8 to 11) were obtained. As in the preparation of a chimeric antibody in the procedure (4), these reshaped V region fragments were digested with HindIII and BamHI restriction enzymes and the VH and VL fragments were incorporated into the HindIII-BamHI site of HCMV-γ1 or HCMV-κ, respectively. Thus, there were prepared μ39.1 reshaped antibody gene expression vectors (RHμ39.1 and RLμ39.1, respectively) and μ5.5 reshaped antibody gene expression vectors (RHμ5.5 and RLμ5.5, respectively).

(7) Expression of anti-HIV reshaped antibody

An activity of antibodies obtained by these reshaped μ39.1 and μ5.5 antibody genes was examined in the above-mentioned transient expression system using COS7 cells. As in the procedure (5), a culture supernatant of the cells where the gene was incorporated was collected and an activity of antibodies present in the culture supernatant was measured by ELISA employing an anti-human IgG or SP-1 peptide. As a result, as shown in FIG. 7, both expression products from a mixture of RHμ39.1 and RLμ39.1 plasmid DNAs and from a mixture of RHμ5.5 and RLμ5.5 plasmid DNAs bound to SP-1 peptide. Accordingly, it was confirmed that, in the amino acid sequences of μ39.1 and μ5.5 as shown in FIGS. 9 to 12, the transplanted CDR regions were the most important region for exerting an anti-HIV activity. From this result, it was confirmed that the genes coding for these regions are a quite useful gene for preparing a recombinant anti-HIV antibody.

We claim:

1. A recombinant H chain of an anti-HIV antibody, comprising an amino acid sequence of a mouse antibody and an amino acid sequence of a human antibody, characterized by frame regions (FR1 to FR4) and complementarity determining regions (CDR1 to CDR3) forming a hybrid mouse-human variable region of the H chain, wherein the complementarity determining regions have the following amino acid sequences:

CDR1: Glu-Tyr-Thr-Met-His (Amino Acids 31–35 of SEQ ID NO:14)
    CDR2: Gly-Ile-Asn-Pro-Asn-Asn-Gly-Asp-Thr-Ser-Tyr-Thr-Gln-Lys-Phe-Lys-Gly (Amino Acids 50–66 of SEQ ID NO:14)
    CDR3: Pro-Tyr-Tyr-Ala-Tyr-Ala-Ile-Asp-Ser (Amino Acids 99–106 of SEQ ID NO:14).

2. The recombinant anti-HIV antibody H chain of claim 1, wherein:

one amino acid at the C terminus of frame region FR1 adjacent to the complementarity determining region CDR1 is threonine;

a two amino acid sequence at the C terminus of FR2 adjacent to CDR2 is Ile-Gly;

a six amino acid sequence at the N terminus of FR3 adjacent to CDR2 is amino acid residues 67–72 of SEQ ID NO:14; and one amino acid at the C terminus of FR3 adjacent to CDR3 is threonine.

3. The recombinant anti-HIV antibody H chain of claim 1, wherein a whole amino acid sequence of a variable region of said antibody is amino acid residues 1 to 118 of SEQ ID NO:14.

4. A recombinant L chain of an anti-HIV antibody, comprising an amino acid sequence of a mouse antibody and an amino acid sequence of a human antibody characterized by frame regions (FR1 to FR4) and complementarity determining regions (CDR1 to CDR3) forming a hybrid mouse-human variable region of the L chain, wherein the complementarity determining regions have the following amino acid sequences:

CDR1: Lys-Ala-Ser-Gln-Ser-Val-Asp-Tyr-Asp-Gly-Asp-Ser-Tyr-Met-Asn (Amino Acids 24–38 of SEQ ID NO:16)

CDR2: Ala-Ala-Ser-Asn-Leu-Glu-Ser (Amino Acids 54–60 of SEQ ID NO:16)

CDR3: Gln-Gln-Ser-Asn-Glu-Asp-Pro-Trp-Thr (Amino Acids 93–101 of SEQ ID NO:16).

5. The recombinant anti-HIV antibody L chain of claim 4, wherein a whole amino acid sequence of a variable region of said antibody is amino acid residues 1 to 111 of SEQ ID NO:16.

6. A recombinant anti-HIV antibody comprising the recombinant anti-HIV H chain of claim 1 and a recombinant anti-HIV antibody L chain comprising an amino acid sequence of a mouse antibody and an amino acid sequence of a human antibody characterized by frame regions (FR1 to FR4) and complementarity determining regions (CDR1 to CDR3) forming a hybrid mouse-human variable region of the L chain, wherein the complementarity determining regions have the following amino acid sequences:

CDR1: Lys-Ala-Ser-Gln-Ser-Val-Asp-Tyr-Asp-Gly-Asp-Ser-Tyr-Met-Asn (amino acids 24–38 of SEQ ID NO:16)

CDR2: Ala-Ala-Ser-Asn-Leu-Glu-Ser (amino acids 54–60 of SEQ ID NO:16)

CDR3: Gln-Gln-Ser-Asn-Glu-Asp-Pro-Trp-Thr (amino acids 93–101 of SEQ ID NO:16), wherein said recombinant anti-HIV antibody has neutralizing activity against human immunodeficiency virus (HIV).

7. A DNA fragment coding for an H chain variable region, or a portion thereof, of an antibody having a neutralizing activity against human immunodeficiency virus (HIV), said DNA fragment consisting of a nucleotide sequence of nucleotide Nos. 1 to 354 in Sequence Listing: SEQ ID NO: 5 or a portion of said nucleotide sequence.

8. A DNA fragment coding for an L chain variable region, or a portion thereof, of an antibody having a neutralizing activity against human immunodeficiency virus (HIV), said DNA fragment consisting of a nucleotide sequence of nucleotide Nos. 1 to 333 in Sequence Listing: SEQ ID NO: 7 or a portion of said nucleotide sequence.

9. A DNA fragment coding for an H chain variable region, or a portion thereof, of an antibody having a neutralizing activity against human immunodeficiency virus (HIV), said DNA fragment consisting of nucleotides 1 to 354 of SEQ ID NO:13, or a portion of said nucleotide sequence.

10. A DNA fragment coding for an L chain variable region, or a portion thereof, of an antibody having a neutralizing activity against human immunodeficiency virus (HIV), said DNA fragment consisting of nucleotides 1 to 333 of SEQ ID NO:15, or a portion of said nucleotide sequence.

* * * * *